United States Patent [19]

Willie

[11] Patent Number: 4,564,270
[45] Date of Patent: Jan. 14, 1986

[54] OBJECTIVE LENS COVER FOR AN OPERATING MICROSCOPE

[75] Inventor: Michael T. Willie, Redding, Conn.

[73] Assignee: Surgikos, Inc., Arlington, Tex.

[21] Appl. No.: 510,494

[22] Filed: Jul. 5, 1983

[51] Int. Cl.[4] ............................................. G02B 21/00
[52] U.S. Cl. .................................................... 350/587
[58] Field of Search ................ 350/257, 318, 585, 587

[56] References Cited

U.S. PATENT DOCUMENTS

| | | | |
|---|---|---|---|
| 3,796,477 | 3/1974 | Geraci | 350/587 |
| 4,266,663 | 5/1981 | Geraci | 350/585 |
| 4,281,895 | 8/1981 | Mohr | 350/257 |
| 4,385,812 | 5/1983 | Wille et al. | 350/587 |

FOREIGN PATENT DOCUMENTS 566242 12/1932 Fed. Rep. of Germany ...... 350/587

OTHER PUBLICATIONS

"Publication 1980", Article on Filter Mounting.

Primary Examiner—William H. Punter
Attorney, Agent, or Firm—Michael Q. Tatlow

[57] ABSTRACT

A disposable operating microscope drape with a replaceable lens cover is disclosed. The lens cover is in a housing which is constructed of a resilient, deformable foam material. The housing can be force fit around the objective lens of the microscope and contains a pocket into which a replaceable lens cover can be inserted to protect the objective lens of the microscope.

4 Claims, 5 Drawing Figures

U.S. Patent   Jan. 14, 1986   Sheet 1 of 2   4,564,270
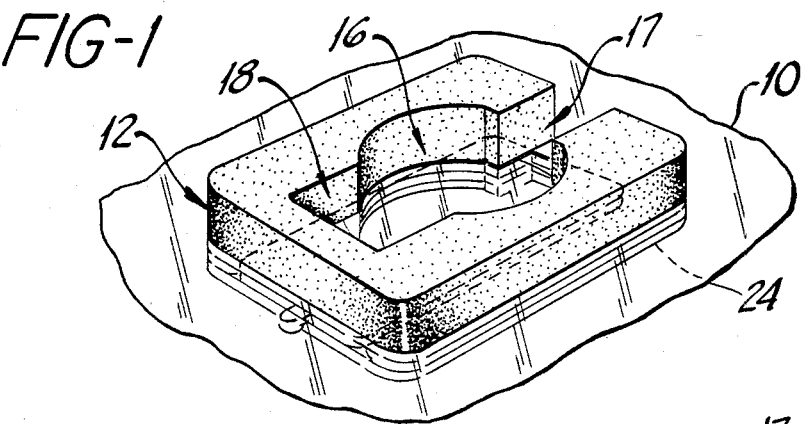
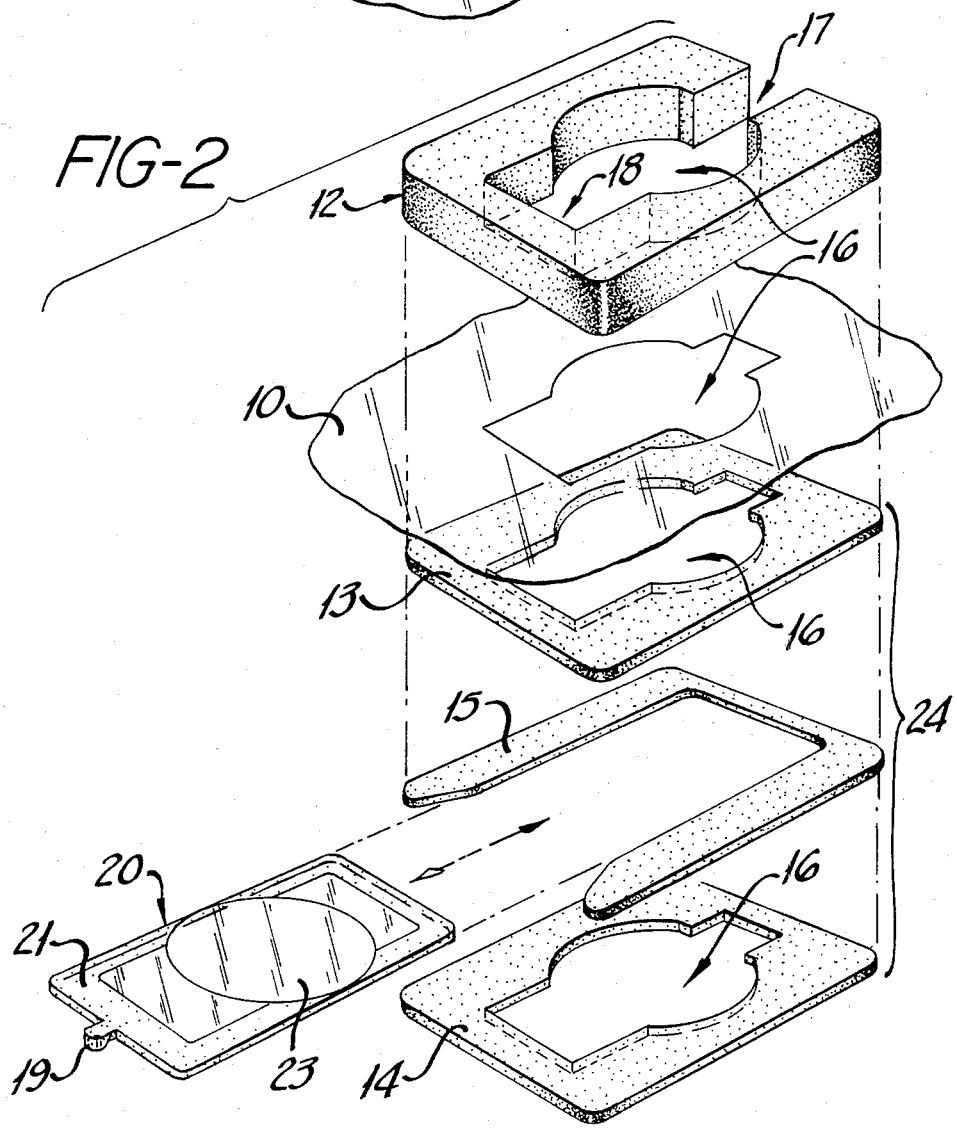

OBJECTIVE LENS COVER FOR AN OPERATING MICROSCOPE

BACKGROUND OF THE INVENTION

1. Field of the Invention

This invention relates generally to lens covers for operating microscopes and, more specifically, to an objective lens cover employed in conjunction with disposable sterile operating microscope drapes.

Operating microscopes are employed in the performance of various surgical procedures. As in any surgical procedure, it is necessary to maintain the operative site in as sterile a condition as possible. Because the microscope used in microsurgery is placed in close proximity to the operative site, the microscope itself is usually draped with a transparent or opaque surgical drape to prevent stray materials, such as dust, from falling from the microscope into the operative field. Since the objective lens of the microscope is placed in close proximity to the operative site, it is necessary to protect the objective lens of the microscope from being smeared with body fluids from the patient or with various solutions which may be used in surgery. In addition, the objective lens covers are used to protect the objective lens of the microscope from the danger of being contacted with a surgical instrument and scratched or otherwise damaged.

Operating room microscope drapes are generally fabricated from plastic materials to completely encase the operating room microscope as well as the structure that is used to support the microscope during the surgical procedure. Prior art microscopes drapes have included objective lens cover assemblies of various configurations, but these prior configurations have not been totally satisfactory. U.S. Pat. No. 3,528,720 to Treace discloses a microscope drape made of a clear plastic envelope which can be fitted over an operating microscope. The drape includes a circular aperture positioned to receive the objective lens of the microscope and an objective lens ring to frictionally fit the objective lens frame on the microscope. The ring is fabricated from a resilient deformable plastic material and is fitted onto the objective lens frame. The structure disclosed in this patent does not include a lens cover but protects the lens from contact by surgical instruments by providing a ring structure 53 which projects downwardly from the point of attachment of the lens ring to the microscope.

U.S. Pat. No. 3,796,477 to Geraci discloses a flexible lens housing which employs a removable lens cover. The lens cover disclosed in Geraci is force-fitted into a notch or groove in the interior of the lens housing. In order to remove the lens cover in the Geraci drape for replacement, it is necessary to deform the lens ring housing or ring and possibly remove the lens ring housing from the microscope. The removal of the lens ring housing from the microscope is not desirable, as particles on the interior portion of the drape might be dislodged during the removal of the lens ring housing and fall into the operative site. In order to replace the lens cover in the Geraci drape, it is necessary to fit a new lens cover into the groove within the lens housing, which is a difficult manipulative procedure considering that it is important not to come into contact or smudge the lens cover, which would possibly distort the image as seen through the lens of the microscope.

The Geraci U.S. Pat. No. 4,266,663 also discloses an operating microscope with a lens cover which, again, is snapfitted into a lens housing and may also be difficult to replace since it must be grasped by the tabs on the lens cover without contacting the central surface of the lens cover.

U.S. Pat. No. 3,698,791 to Walchle et al. also discloses a microscope drape with an integral lens cover secured in the drape. The lens housing in the Walchle et al. reference frictionally engages the objective lens through an aperture in the drape. The housing is made of a cross-linked polyethylene foam which is secured to the drape with a pressure sensitive adhesive. The lens cover in the drape of Walchle et al. is not replaceable, and, if the cover is smeared, it would be necessary to change the entire drape.

The lens cover of the present invention overcomes the problems with the prior art lens covers and also provides a lens cover which may be used with an illuminating microscope. In an illuminating microscope, there is a source of light, either through a fiberoptic device or through a direct light source, which is positioned in proximity to the objective lens. The surgical drapes in the above-mentioned references are not capable of providing access of this light source through a lens cover, and these drapes may not be used with microscopes with illuminating sources adjacent the objective lenses.

SUMMARY OF THE INVENTION

The present invention provides a lens cover for an operating microscope drape which can be readily changed. With the present cover there is little tendency for the operating room personnel to come in contact with the portion of the lens cover which is placed in front of the objective lens of the microscope. In addition, the lens cover housing may be readily adapted to be used with operating microscopes which use illuminators adjacent the objective lens.

The lens housing in the present invention is fabricated in the form of a rectangle made from a crosslinked polyethylene foam or other foam material and is constructed in the form of a sandwich with a pocket or slot in one side of the housing into which a generally rectangular objective lens cover can be placed. The lens cover can be readily removed and replaced if necessary.

DESCRIPTION OF THE DRAWINGS

FIG. 1 is a perspective view of the objective lens cover of the present invention.

FIG. 2 is an exploded view of the lens housing of the present invention showing the various components of the housing.

DETAILED DESCRIPTION OF THE INVENTION

Figure 3:
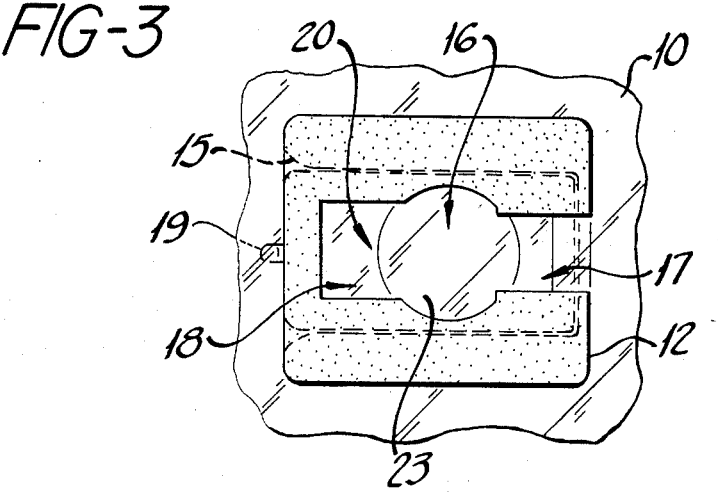
FIG. 3 is a top view of the lens housing of the present invention.

The invention will be better understood with reference to the drawings and, particularly, FIG. 2. The lens housing is made in two portions, a microscope contact portion 12 and a lens cover receiving portion 24. These portions are secured in alignment on opposite sides of the microscope drape 10. Each of the sections of the lens cover housing is made from a resilient foam material which is capable of being deformed to be force-fitted onto the objective lens ring of the microscope. Foams that has been found to be particularly advantageous are a crosslinked polyethylene foam or a polyester urethane foam. The microscope contact portion 12 of the lens housing is that portion which actually contacts the objective lens ring of the microscope. This portion is considerably thicker, three to five times thicker, than the lens cover receiving portion 24 of the lens housing to provide a friction fit to the objective lens ring. The surgical drape 10 is placed between the portion 12 and the portion 24 and is adhesively secured to those sections of the housing. The adhesive may be directly applied to the surface of the sections or it may be applied in the form of a double-faced adhesive tape. The lens cover receiving portion 24 is preferably constructed from three separate pieces or segments of foam material. The first segment 13 and the third segment 14 are generally identical and have the configuration as shown in the drawing. The second segment 15 is a spacer and is positioned between the first segment 13 and the third segment 14 to create a slot or pocket to receive the lens cover 20. The spacer or second segment 15 is as thick as the lens cover. The spacer segment has a U-shaped opening or slot, shown in the drawings, which is capable of receiving a generally rectangular lens cover 20. The spacer segment 15 can be impregnated with adhesive to secure it to the first and third segments (13, 14) of the lens receiving portion of the housing. There is a circular aperture through all the components of the lens housing, as shown in the drawings. This aperture is generally equal in size to the outside diameter of the objective lens housing of the microscope. As shown in FIGS. 1–4, there are rectangular sections 17 and 18 which are contiguous to the central circular aperture 16. These rectangular portions 17 and 18 are employed in lens covers for illuminating microscopes and provide space for the light sources of the microscopes to project their illumination through the lens housing. As shown in the drawing, the rectangular section 17 extends to the edge of the microscope contact portion of the housing and provides space for a fiber light cable or electrical power cable. The lens cover 20 is made of clear polystyrene, an acrylic plastic material or may be made of glass. As shown in FIG. 2, there is a generally circular portion 23 of the lens cover which generally corresponds to the area of the objective lens of the microscope. The perimeter of the objective lens cover may have a roughened surface 21 which assists in maintaining the lens cover within the slot in the housing. There is a tab 19 integrally molded onto the plastic lens cover or attached to a glass lens cover to enable the operating room personnel to grasp the lens cover and remove it from the lens housing. In place of the tab 19, the lens cover may be longer than the U-shaped opening so that a portion of the lens cover will extend beyond the housing to provide a surface to grasp for removal of the lens cover.

In the preferred embodiment of the invention, the lens contacting portion 12 of the housing is approximately three-quarters of one inch thick. This thickness is sufficient to firmly seat the lens cover housing on the objective lens of an operating microsocpe. The thickness of the lens cover receiving portion of the housing is approximately five-sixteenths of one inch, with the first and third segments (13,14) being about one-eighth of an inch thick, and the spacer segment 15 being about one-sixteenth of one inch thick.

Figure 4:
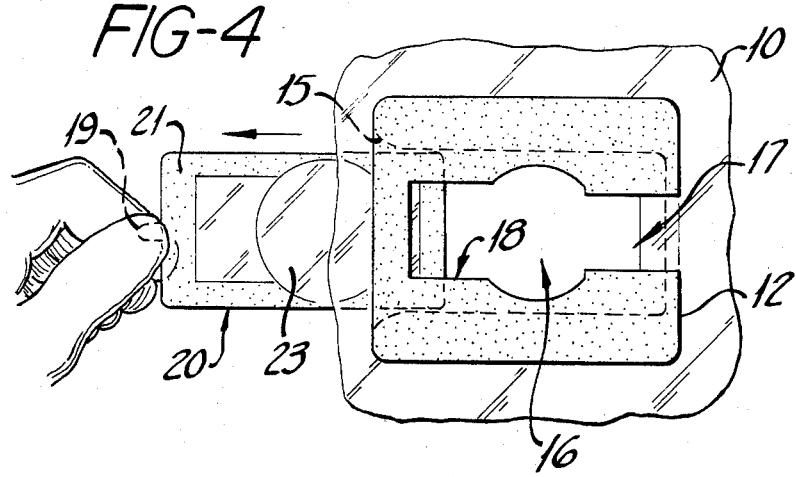
FIG. 4 is a view showing the removal of the objective lens cover from the housing.

FIG. 3 shows a top view of the lens housing with the lens cover in place. FIG. 4 shows how the lens cover can be readily removed from the housing if it is necessary to replace the lens cover during the surgical procedure.

Figure 5:
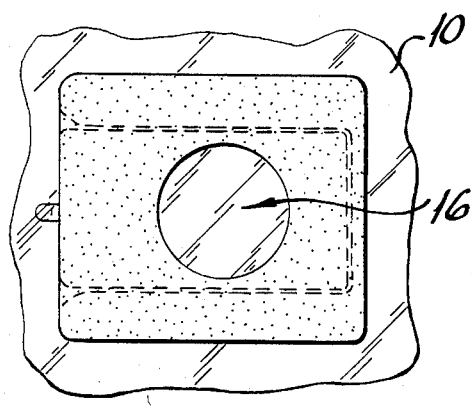
FIG. 5 is a top plan view of a different embodiment of the present invention.

The embodiment of the present invention shown in FIG. 5 is of the identical construction as that shown in FIG. 2 but without the rectangular sections 17 and 18 removed from the foam material. This construction can be used in a drape for a standard microscope that does not use illuminators adjacent to the objective lens of the microscope.

The lens cover may be readily removed and replaced in the construction of the present invention without fear of the operating room personnel contacting that portion of the lens cover which would be in front of the objective lens of the microscope. In addition to the tab 19 which can be grasped by the person replacing the lens, there is sufficient room in the objective lens cover away from the circular portion 23 to allow the lens cover itself to be grasped if necessary without smudging or smearing that portion of the lens cover which is in front of the objective lens of the microscope.

I claim:

1. A disposable microscope drape for enclosing an operating microscope and having an objective lens cover secured thereto, the improvement comprising said lens cover being secured in a housing, said housing comprising a first lens contacting portion composed of a flexialbe, deformable, resilient material having a circular opening capable of being force-fitted over the objective lens ring of an operating microscope, a second portion having the same outside dimensions as said first portion sand having a circular opening aligned with the circular opening of said first section, the operating microscope drape being adhesively secured between said first and second portions, said second portion having a pocket section, a rectangular lens cover removably fitted into the pocket in the second portion and a rectangular cutout on both sides of the circular opening in the housing to provide openings for external illuminators adjacent the objective lens of the microscope.

2. The disposable drape of claim 1 in which the first and second portions of the lens cover housing and are composed of a crosslinked polyethylene foam.

3. The disposable drape of claim 1 in which the thickness of the first portion is three to five times the thickness of the second portion.

4. The disposable drape of claim 1 in which the pocket is formed by a U-shaped spacer element secured between two rectangular segments of foam of the same configuration as the lens contacting portion.

* * * * *